United States Patent [19]

Thacker

[11] Patent Number: 5,176,138
[45] Date of Patent: Jan. 5, 1993

[54] IMPLANTABLE PACEMAKER HAVING MEANS FOR AUTOMATICALLY ADJUSTING STIMULATION ENERGY AS A FUNCTION OF SENSED $SO_2$

[75] Inventor: James R. Thacker, Lake Jackson, Tex.

[73] Assignee: Siemens Pacesetter, Inc., Sylmar, Calif.

[21] Appl. No.: 672,810

[22] Filed: Mar. 21, 1991

[51] Int. Cl.⁵ ............................................. A61N 1/362
[52] U.S. Cl. ............................................. 128/419 PG
[58] Field of Search ................................ 128/419 PG

[56] References Cited

U.S. PATENT DOCUMENTS

| | | | |
|---|---|---|---|
| 3,777,762 | 12/1973 | Nielsen | 128/419 P |
| 4,202,339 | 5/1980 | Wirtzfeld et al. | 128/419 PG |
| 4,399,820 | 8/1983 | Wirtzfeld et al. | 128/419 PG |
| 4,686,988 | 8/1987 | Sholder | 128/419 PT |
| 4,712,555 | 12/1987 | Thornander et al. | 128/419 PG |
| 4,750,495 | 6/1988 | Moore et al. | 128/419 PG |
| 4,791,935 | 12/1988 | Baudino et al. | 128/637 |
| 4,809,697 | 3/1989 | Causey et al. | 128/419 PT |
| 4,815,469 | 3/1989 | Cohen et al. | 128/634 |
| 4,940,052 | 7/1990 | Mann et al. | 128/419 PG |
| 4,944,299 | 7/1990 | Silvian | 128/419 PG |

OTHER PUBLICATIONS

"A Practice of Cardiac Pacing", Furman et al., Futura Publishing Co., Mt. Kisco N.Y., 1986 pp. 27-73.

Primary Examiner—Kyle L. Howell
Assistant Examiner—Scott M. Getzow
Attorney, Agent, or Firm—Bryant R. Gold; Leslie S. Miller

[57] ABSTRACT

An implantable programmable pacemaker includes a sensor for measuring $SO_2$ levels in blood on a periodic basis, e.g., every 15 seconds, while the pacemaker is operating in its programmed mode of operation. The energy of stimulation pulses generated by the pacemaker is automatically adjusted, as required, in order to maintain a prescribed level of $SO_2$ in the blood. At least a minimum level of $SO_2$ is presumed when the stimulation pulses are of sufficient energy to effectuate capture. Hence, the $SO_2$ level is monitored to provide an indication of whether capture has been lost, and if so, to increase the stimulation energy. In one embodiment, the stimulation energy is increased by first increasing the pulse width of the stimulation pulse a prescribed amount. After the pulse width has been increased a maximum amount, and if capture is still lost, the stimulation energy is further increased by increasing the pulse amplitude a prescribed amount. After the pulse amplitude has been increased a maximum amount, and if capture is still lost, the operating mode of the pacemaker is changed, and the stimulation energy is reset to an appropriate value.

25 Claims, 3 Drawing Sheets

IMPLANTABLE PACEMAKER HAVING MEANS FOR AUTOMATICALLY ADJUSTING STIMULATION ENERGY AS A FUNCTION OF SENSED SO$_2$

BACKGROUND OF THE INVENTION

The present invention relates to implantable pacemakers, and more specifically to an implantable pacemaker having means for automatically adjusting the stimulation pulse energy so as to efficiently maintain capture.

A pacemaker is an implantable medical device which delivers electrical stimulation pulses to a patient's heart in order to keep the heart beating at a desired rate. The electrical stimulation pulse, when of sufficient energy, depolarizes the cardiac tissue whereat the pulse is applied, causing such tissue to contract. Some pacemakers, and some pacemaker operating modes, provide stimulation pulses at a fixed rate or frequency, such as 70 pulses per minute, thereby maintaining the heart beat at that fixed rate. Other pacemakers, and other pacemaker operating modes, further monitor the heart to determine if the heart is beating on its own (a "natural heart beat"), without being stimulated by a stimulation pulse. If a natural heart beat is detected within a prescribed time period (typically referred to as the "escape interval"), no stimulation pulse is delivered, thereby allowing the heart to beat on its own without consuming the limited power of the pacemaker. (Each stimulation pulse generated by the pacemaker represents an expenditure of energy from the pacemaker's limited power source.) Such pacemakers, and pacemaker modes, are known as "demand pacemakers" because stimulation pulses are provided only as demanded by the heart.

Pacemakers are known that deliver stimulation pulses, and monitor cardiac activity, in the atrium and/or the ventricle of a mammalian heart. Regardless, however, of whether a pacemaker stimulation pulse is applied to the heart atrium or the heart ventricle, the heart must respond to the stimulus provided, or else the energy in the pulse serves no useful purpose, and in fact represents a needless depletion of the limited energy store within the pacemaker. If the stimulation pulse is of sufficient energy to cause depolarization of cardiac tissue, the pulse is said to "capture" the heart. If the stimulation pulse is not of sufficient energy to cause depolarization, the pulse does not capture the heart. "Capture" is thus defined as a cardiac response to a pacemaker stimulation pulse.

Every patient has a threshold which is generally defined as a minimum amount of stimulation energy required to effectuate capture. It is usually desired to achieve capture at the lowest possible energy level setting (in order to conserve energy) yet provide enough of a safety margin so that should the patient's threshold increase, the output of the implanted pacemaker is still sufficient to maintain capture.

Capture is usually determined by means of an electrocardiogram (ECG) measured through ECG electrodes placed on the patient's limbs and/or chest. Some modern implanted pacemakers, electromagnetically coupled to an external programming device, provide an intracardiac ECG without the need for ECG electrodes. When a patient is connected to a typical ECG monitor, or when the patient has one of the newer pacemakers having intracardiac ECG capabilities coupled to an appropriate programming and viewing device, and when the pacemaker is providing stimulation pulses, the physician monitors the output to assess whether each pacing pulse, which is seen as a spike or other marker on the ECG, is followed by a cardiac response. All modern implantable pacemakers are "programmable," meaning that selected operating parameters associated with the pacemaker can be set to a desired value using appropriate noninvasive programming techniques. The amplitude and/or pulse width of the stimulation pulse are typical parameters that can be programmed in this manner. See, e.g., Furman et al., *A Practice of Cardiac Pacing*, pp 39–55 (Futura Publish Co., 1986). Thus, through experimenting with various settings of the stimulation pulse amplitude and pulse width while viewing the cardiac ECG, the physician is able to determine the approximate "threshold" at which capture occurs. Once this threshold is determined, the physician typically programs the stimulation pulse energy to a level well above the threshold level so as to provide an adequate safety margin.

One type of pacemaker known in the art includes a special calibration mode wherein a series of stimulation pulses of increasing amplitude are generated. Thus, by monitoring the ECG waveform at the same time that this series of increasing amplitude or increasing pulse width stimulation pulses is being applied to the heart, and knowing the approximate amplitude of each stimulation pulse in such sequence, the physician can readily determine the appropriate capture threshold level. See U.S. Pat. No. 3,777,762.

In all of these techniques for determining the capture threshold, and setting the appropriate stimulation energy, it is necessary for the pacemaker patient to physically interact with the physician, which interaction requires time and expense on the part of both the patient and physician. That is, the patient must make the necessary arrangements (and incur the corresponding expenses) of traveling to visit the physician. Likewise, the physician must acquire and set up special monitoring equipment in order to examine the ECG data of the patient. The physician must then manually program the stimulation energy to a level that is well above the determined capture threshold. Usually, due to the imprecise method used to determine the capture threshold, as well as the changes that may occur in the capture threshold over time, a safety factor of at least two is incorporated into the setting of the stimulation energy. Thus, it is quite common for the stimulation energy to be set twice as high as it actually needs to be set. Such a high energy setting depletes the limited energy available within the pacemaker more than is necessary. Further, because the capture threshold may change significantly for a given patient over time and for differing physiological conditions, all of the above steps must be repeated on a regular basis.

What is needed, therefore, is a less bothersome, and less expensive, technique for determining the capture threshold, as well as a more precise manner of setting the stimulation energy so as not to expend more energy than is required. What is also needed is a pacemaker wherein the stimulation energy can be automatically adjusted as required in order to adapt to changing capture thresholds.

SUMMARY OF THE INVENTION

The present invention advantageously provides an implantable pacemaker that addresses the above, and other, concerns. For example, the present invention provides a pacemaker that not only includes a simpler, less bothersome, less expensive, and more reliable technique for determining the cardiac capture threshold, but also provides a means for automatically adjusting the stimulation pulse energy to automatically adapt to changes in the capture threshold. Thus, the amount of energy expended in the stimulation pulses is automatically adjusted to a level that is only as high as is required in order to maintain capture, while still maintaining an adequate margin of safety.

In accordance with one aspect of the present invention, a sensor that measures the amount of saturated oxygen ($SO_2$) in the blood of a patient, is coupled to a programmable pacemaker that has been implanted in the patient. The $SO_2$ measurement is made on a periodic basis while the pacemaker is operating in its programmed mode of operation. The energy of the stimulation pulses generated by the pacemaker is automatically adjusted, as required, in order to maintain a prescribed level of $SO_2$ in the blood.

In accordance with another aspect of the invention, a technique or method for determining and automatically maintaining cardiac capture is provided. Such technique or method is based on the presumption that at least a minimum level of $SO_2$ will be present in the blood of a pacemaker patient so long as the pacemaker is able to maintain capture. That is, if the heart is beating at a normal rate, whether naturally or as stimulated by the pacemaker, the oxygen-carrying blood from the lungs will be circulated throughout the patient's body and the level of $SO_2$ in the blood will remain above certain levels. Should the heart stop beating at a normal rate, however, as would occur if capture is lost, then the blood is not circulated as efficiently as it should be, and the level of $SO_2$ in the blood drops significantly. Hence, in accordance with this aspect of the invention, the blood $SO_2$ level is monitored to provide an indication of whether capture has been lost, and if so, to automatically increase the stimulation energy of the pacemaker pulses in an attempt to regain capture.

In one embodiment of the invention, the stimulation energy is increased by first increasing the pulse amplitude of the stimulation pulses in discrete increments, one increment at a time. As soon as capture is regained, no further increases in the pulse amplitude are made. Should capture still be lost (i.e., should the sensed $SO_2$ levels remain less than a prescribed reference value) after the pulse amplitude has been increased in discrete steps up to a maximum level, the stimulation energy is further increased by increasing the pulse width in discrete increments, one increment at a time. Should capture still be lost after the pulse width has been increased in discrete steps up to a maximum width, the operating mode of the pacemaker is automatically changed, and the stimulation energy may be reset to its original value.

The invention may thus be characterized as an implantable pacemaker that includes means for automatically adjusting the energy of its stimulation pulse as a function of the amount of $SO_2$ sensed in the blood of the pacemaker patient. Such pacemaker includes: (1) electronic circuit means housed within an implantable case for generating a stimulation pulse having a prescribed pulse amplitude and pulse width in response to a trigger signal; (2) lead means secured to the implantable case and electrically connected to the electronic circuit means for delivering the stimulation pulse to a desired stimulation location of the user's heart; (3) sensor means for sensing $SO_2$ in the blood of the user; and (4) control means for generating the trigger signal in accordance with a prescribed pacemaker mode of operation. The control means includes means for altering the energy of the stimulation pulse by changing at least one of the prescribed pulse amplitude or pulse width as a function of the amount of $SO_2$ sensed by the sensor means.

The invention may also be characterized as a programmable implantable pacemaker that includes conventional pulse generating means for providing a stimulation pulse on demand, where the stimulation pulse has an initial programmed pulse amplitude and pulse width, and hence an initial programmed energy. Also included in the pacemaker are conventional delivery means for delivering the stimulation pulse to at least one of the atrial or ventricular chambers of a mammalian heart in accordance with a programmed mode of operation; and control means for operating the pacemaker in accordance with the programmed mode of operation. The pacemaker further includes sensor means for measuring the $SO_2$ level of the blood within or near the heart every T1 seconds, where T1 is a programmed timed interval. Finally, the pacemaker includes adjustment means for automatically increasing the programmed energy associated with the stimulation pulse in the event that the measured $SO_2$ level is less than a prescribed reference at the conclusion of the programmed timed interval T1. Thus, in operation, such pacemaker adjusts the energy of the stimulation pulse to be only as high as is necessary to maintain a level of $SO_2$ in the blood that is at least equal to the prescribed reference level.

Further, the invention may be viewed as a method of determining and maintaining capture in a programmable implantable pacemaker using a minimum expenditure of energy. The pacemaker used with such method has means for providing a stimulation pulse on demand, this stimulation pulse having an initial programmed pulse amplitude and pulse width, and hence an initial programmed energy. The pacemaker used with the method further has means for delivering the stimulation pulse to at least one of the atrial or ventricular chambers of a mammalian heart in accordance with a programmed mode of operation. Finally, the pacemaker used with such method must also have means for measuring the $SO_2$ level of the blood in or near the mammalian heart. The method comprises: (a) operating the pacemaker in accordance with the programmed mode of operation; (b) measuring the $SO_2$ level of the blood within or near the mammalian heart every T1 seconds, where T1 is a programmed time interval; and (c) automatically increasing the programmed energy associated with the stimulation pulse in the event that the measured $SO_2$ level is less than a prescribed reference level. An $SO_2$ level less than the prescribed reference level is presumed to indicate a noncapture condition. Hence, by adjusting the energy of the stimulation pulse to be only as high as is necessary to maintain an $SO_2$ level above the prescribed reference level, the stimulation energy remains only just as high as is necessary to maintain capture.

It is thus a feature of the invention to provide an implantable pacemaker that automatically adjusts the energy of its stimulation pulse only as high as is required to maintain capture, thereby maintaining capture with a minimum expenditure of energy. It is a related feature of the invention to provide a method for determining capture that is both easy to implement and inexpensive to carry out. The invention does this while providing a pacemaker that determines capture by monitoring the $SO_2$ level in the blood of the pacemaker user.

The pacemaker of the invention thus includes an $SO_2$ sensor, and is operated so that the stimulation pulse energy is automatically adjusted so as to maintain the level of $SO_2$ in the blood of a user of the pacemaker above a preselected level.

It is a further feature of the invention to provide a pacemaker that automatically adjusts the stimulation pulse energy in discrete steps in accordance with a preselected pattern that adjusts the stimulation pulse amplitude and/or pulse width only as required in order to achieve and maintain capture.

It is a related feature of the invention to provide such a pacemaker (wherein the stimulation energy is increased in discrete steps) that increases the stimulation pulse energy by: (1) increasing the width of the stimulation pulse in discrete steps up to a maximum value; and (2) if such energy increase is still insufficient to effectuate capture, increasing the amplitude of the stimulation pulse in discrete steps up to a maximum value.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

Figure 1:
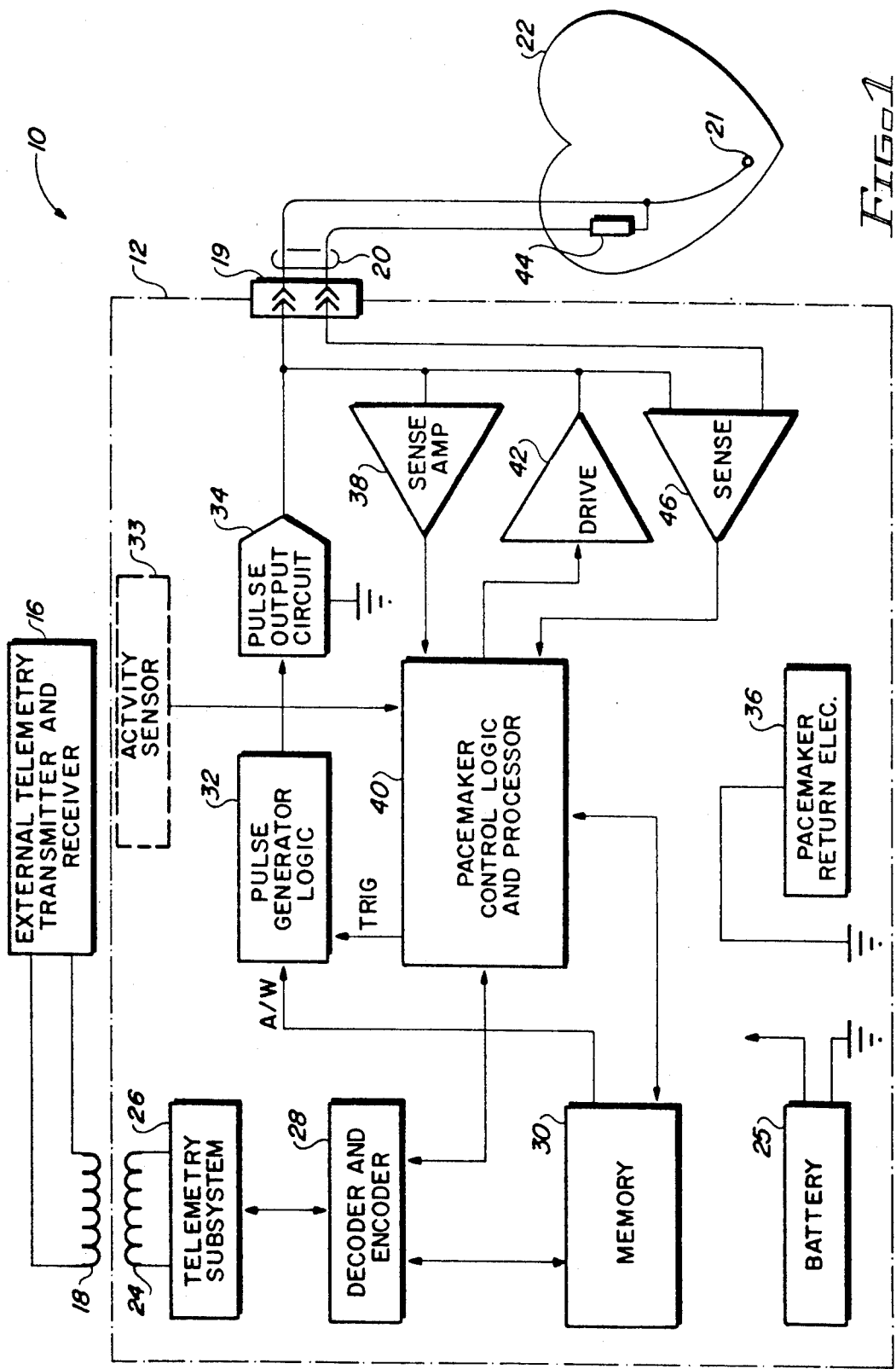
FIG. 1 is a block diagram of an implantable pacemaker made in accordance with the present invention.

The following description is of the best mode presently contemplated for carrying out the invention. This description is not to be taken in a limiting sense, but is made merely for the purpose of describing the general principles of the invention. The scope of the invention should be determined with reference to the claims.

The invention is best understood with reference to the drawings, wherein like reference characters are used to refer to like parts throughout.

With reference to FIG. 1, there is shown a block diagram of an implantable pacemaker 10 made in accordance with the present invention. The pacemaker 10 includes a housing or case 12 adapted to be implanted within a patient. Except for a pacemaker lead 20, all of the circuits of the pacemaker, including a suitable battery 25, are housed within the case 12. The case 12 is electrically insulated with a suitable covering. The pacemaker lead 20 is detachably secured to the circuits of the pacemaker 10 through a suitable connector 19 mounted in the pacemaker case 12. The lead 20 includes at least one electrode 21 that is positioned within a desired chamber of a patient's heart 22. Stimulation pulses are delivered to the heart through the lead 20 and the electrode 21. Further, through the lead 20 and the electrode 21 cardiac activity (e.g., the occurrence of a P-wave, representing the depolarization of the atrium; or the occurrence of an R-wave, representing the depolarization of the ventricle) is sensed. A return electrical path is typically provided through a return electrode 36, which return electrode comprises an exposed (noninsulated) portion of the case 12.

At this point, it should be noted that what is shown in FIG. 1 represents unipolar pacing (i.e., the stimulation pulse is provided through the electrode 21, with an electrical return being provided through body fluids to the return electrode 36) in a single chamber of the heart. It is to be understood, however, that the present invention may also be used using pacemaker configurations that utilize bipolar leads (two spaced-apart electrodes near the distal tip of the lead, with the stimulus being provided through one electrode and the return being provided through the other), or multi-polar leads (multiple electrodes spaced along the length of the lead). Further, the invention may be used for pacing configurations that include pacing in both chambers of the heart. Such alternate pacing configurations are well known in the art See, e.g., U.S. Pat. No. 4,712,555 (the '555 patent) which shows a pacing configuration that paces and senses in both chambers of the heart. The '555 patent also provides a good summary of pacemaker operation, particularly a rate-responsive pacemaker, particularly the manner in which such a pacemaker interfaces with the various signals that may be manifest during a typical cardiac cycle. The '555 patent is incorporated herein by reference in its entirety.

Still referring to FIG. 1, an $SO_2$ sensor 44, may be included as part of the lead 20. Alternatively, the sensor 44 may be provided separate from the lead 20. In either event, the sensor 44 is also detachably secured to the pacemaker circuits through the connector 19, or equivalent, and is positioned so as to be in contact with the patient's blood. The sensor 44 thus provides a means for making an $SO_2$ measurement of the blood. Typically, the sensor 44 is positioned in or near the heart 22, e.g., so as to measure the $SO_2$ level of the blood in the atrium.

The $SO_2$ sensor 44 may be constructed and incorporated within the lead 20 as described in U.S. Pat. No. 4,815,469 (the '469 patent), which patent is assigned to the same assignee as is the present application. The '469 patent is incorporated herein by reference in its entirety. The manner of using such a sensor to sense $SO_2$ levels is also described in the '469 patent. Basically, such a sensor is an optical device that generates light of a prescribed wavelength, directs the light into the blood, and measures the amount of light reflected from the blood. The amount of light reflected provides a measure of the $SO_2$ levels in the blood.

The pacemaker circuits include a telemetry subsystem 26, coupled to a receiving or transmitting coil 24. When data or other commands are to be transferred to the pacemaker 10, or when data (such as intracardiac ECG data) is to be transferred from the pacemaker 10, an external (nonimplanted) coil 18 is positioned adjacent the implanted coil 24. The external coil 18 is coupled to an external telemetry transmitter and receiver 16. The external transmitter and receiver 16 is sometimes referred to as an external "programmer," because it is through use of such device that the implantable pacemaker is programmed to operate in an appropriate mode. However, the external "programming" device 16 typically performs many more functions that just programming, as it also is used to receive data from the pacemaker, both intracardiac data (such as P-waves and R-waves) as well as status data indicating various parameters associated with the pacemaker operation. The device 16 usually includes means for displaying such data in an easy-to-understand and -read format. A more complete description of a typical programming device 16 may be found, e.g., in U.S. Pat. No. 4,809,697.

Still referring to FIG. 1, the telemetry subsystem 26 is coupled to an appropriate decoder and encoder circuit 28. It is the function of the decoder/encoder 28 to decode data received from the telemetry subsystem 26 (which data is encoded for telemetry purposes using an appropriate encoding scheme), and to encode data being sent to the telemetry subsystem 26. A representative telemetry system that may be used in the pacemaker 10 is disclosed, e.g., in U.S. Pat. No. 4,994,299, assigned to the same assignee as is the present application, and incorporated herein by reference. Received data may be stored directly in memory circuits 30, or sent to the pacemaker control logic and processor circuits 40. Similarly, transmitted data may be obtained from the memory circuits 30 or the pacemaker control logic and processor circuits 40.

As are included in all pacemakers, the pacemaker 10 further includes pulse generator logic 32 and pulse output circuits 34. The pulse generator logic receives a trigger signal, or equivalent, from the control logic/processor circuits 40 whenever the pacemaker is to generate a stimulation pulse. Pulse amplitude and width (A/w) data are obtained from the memory circuits 30. Acting on this information, the pulse generator logic 32 drives the pulse output circuit(s) 34 so as to cause a stimulation pulse of the specified pulse amplitude and width to be generated and delivered to the lead 20, and ultimately to the heart 22.

Activity of the heart, e.g., a P-wave (evidencing contraction of the atrium) or an R-wave (evidencing contraction of the ventricle) is sensed through the electrode 21 and lead 20 through sense amplifier(s) 38. In normal demand-mode operation, the sensing of a naturally occurring heartbeat through the sense amplifier(s) 38 within a prescribed time period inhibits the control logic/processing circuits 40 from generating the trigger signal that causes a stimulation pulse to be generated by the pulse generator logic circuit 32 and the pulse output circuit(s) 34.

The pacemaker 10 may also include an activity sensor 33. The activity sensor 33 generates a signal representative of some parameter indicative of physiological activity. For example, the sensor 33 may comprise a piezoelectric crystal that generates an electrical signal indicative of the physical activity (movement) of the sensor. Such signal is utilized by the pacemaker to automatically adjust the rate at which the pacemaker provides stimulation pulses on demand. When a sensor 33 is used in this manner, the pacemaker 10 is known as a "rate-responsive" pacemaker, capable of adjusting the pacing rate in order to suit the sensed physiological needs of the patient. Rate-responsive pacemakers are known in the art. See, e.g., U.S. Pat. Nos. 4,485,813; 4,940,052; and 4,940,053. The '052 and '053 patents are assigned to the same assignee as is the instant application, and are incorporated herein by reference. Advantageously, the present invention may be used with rate-responsive pacemakers just as easily as it may be used with nonrate-responsive pacemakers.

As described thus far, the pacemaker 10 is substantially the same as pacemakers of the prior art. However, a significant difference between the pacemaker 10 and pacemakers of the prior art is the use of the $SO_2$ sensor 44, including an $SO_2$ drive circuit 42 and an $SO_2$ sense amplifier 46, and the use of the output signal of the $SO_2$ sense amplifier 46 as an indicator of whether or not "capture" is present. This "captive" determination is carried out as shown below in FIGS. 2 and 3.

Figure 2:
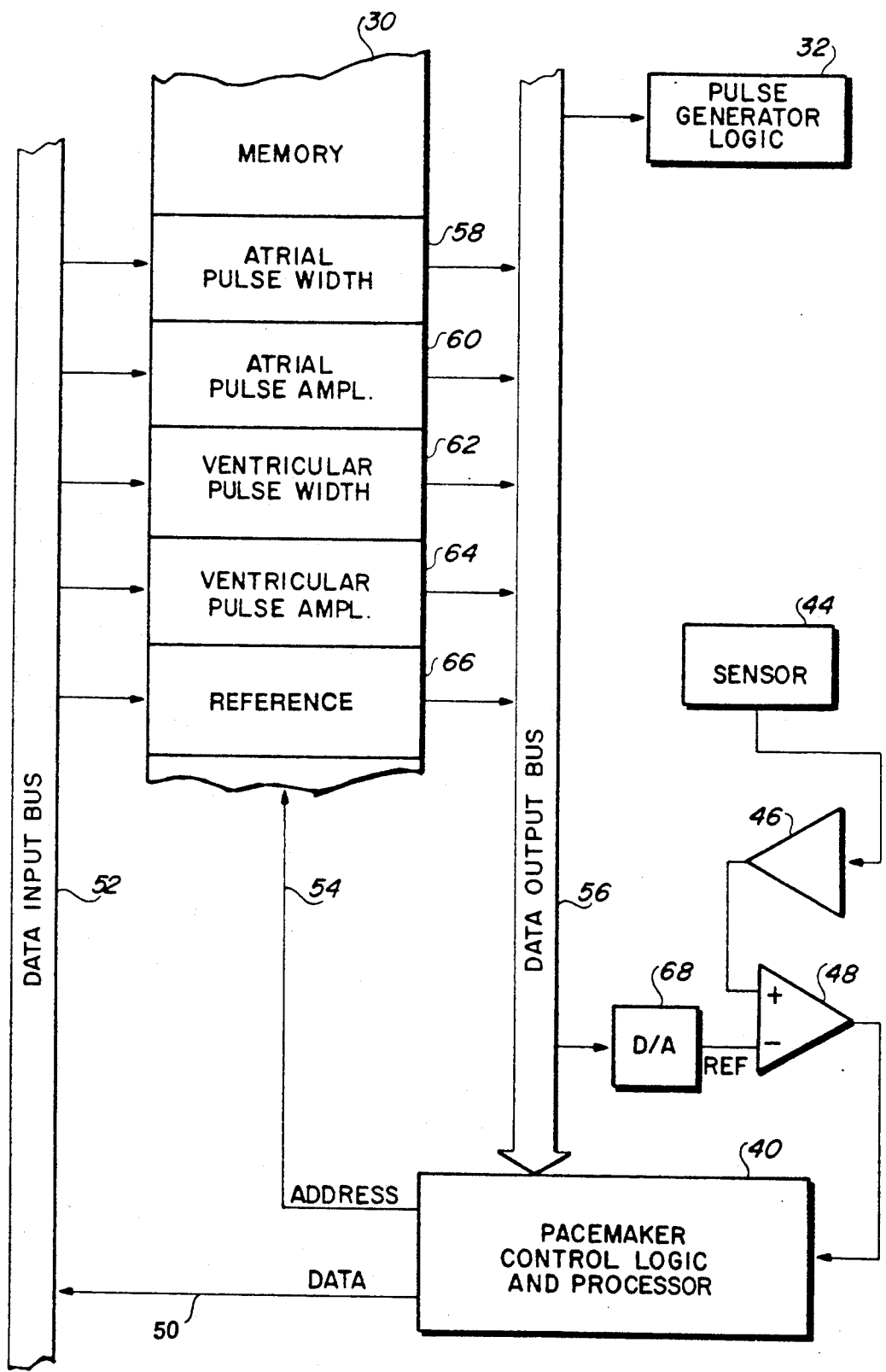
FIG. 2 is a functional block diagram depicting various control parameters stored in the memory of the implantable pacemaker of FIG. 1, showing how these control parameters are used to control the operation of the pulse generator logic, and also showing how the sensed value of $SO_2$, if less than a set reference value, causes the stored values of some of these control parameters to be changed.

FIG. 2 is a functional block diagram depicting various control parameters stored in the memory 30 of the implantable pacemaker of FIG. 1. Included among these control parameters, for example, is a data word, stored in a specific memory location 58 of the memory 30, that defines the pulse width of an atrial stimulation pulse. Another data word stored in memory location 60, defines the pulse amplitude of an atrial stimulation pulse. Likewise, a data words stored in memory locations 62 and 64 respectively define the pulse width and pulse amplitude of a ventricular stimulation pulse. Another data word, stored in memory location 66 of the memory 30, defines a reference $SO_2$ value. All of these control parameters (data words) stored in the memory 30 are initially stored or loaded therein using conventional programming techniques as taught, e.g., in U.S. Pat. No. 4,232,679.

The memory 30 includes a data input bus 52 and a data output bus 56. Further, an address bus 54, or equivalent, allows any data location within the memory 30 to be accessed over the data input bus 52 in order to "write" (store) a particular data word in the addressed memory location. Similarly, by specifying the particular address of a memory location whereat desired data is located, such data can be "read" (copied) onto the data output bus and made available for use by another circuit. (Those of skill in the art will readily recognize that some memory configurations use the same data bus as the data input bus 52 and the data output bus 56. That which is shown in FIG. 2 is therefore merely functional of numerous memory configurations known in the art that could be used. Any of these known memory configurations may be used for purposes of the present invention. All of these memory configurations include some means for addressing specific memory locations, and writing data thereto, or reading data therefrom.)

In accordance with the present invention, the data word defining the appropriate (atrial or ventricular) pulse width and amplitude is made available, over the data output bus 56, to the pulse generator logic 32 as controlled by the control logic/processor 40. The pulse generator logic 32 then converts this data into appropriate signals so as to cause the pulse output circuit 34 (FIG. 1) to generate a stimulation pulse of the desired amplitude and width.

Also, in accordance with the present invention, the data word defining the $SO_2$ reference level, stored in memory location 66, is made available over the output data bus to the comparator circuit 48, as controlled by the control logic/processor 40. As shown in FIG. 2, this data word is first presented to a digital-to-analog (D/A) converter 68 and then presented to the negative input of comparison amplifier 48. The positive input to the comparison amplifier 48 is connected to the output of the $SO_2$ sense amplifier 46. Hence, whenever the $SO_2$ signal at the output of the $SO_2$ sense amplifier 46 is greater than the $SO_2$ reference level, the output of the comparison amplifier 48 is high. However, should the $SO_2$ signal go lower than the $SO_2$ reference level, then the output of the comparison amplifier 48 goes low. Thus, the control logic/processor 40, by monitoring whether the output of the comparison amplifier 48 is high or low, is able to determine whether the $SO_2$ signal is less than or greater than the $SO_2$ reference level, and hence whether or not the stimulation pulse energy (pulse amplitude and/or pulse width) is of sufficient magnitude to effectuate capture.

It is again emphasized that what is shown in FIG. 2 is functional, and is presented as shown because it is easiest to understand. In practice, the function of the comparison amplifier 48 is most easily carried out digitally within the processing circuits of the control logic/processor 40. In such a case, the output of the $SO_2$ sensor 44, after appropriate amplification and/or buffering in the sense amplifier 46, is converted to an equivalent digital signal, i.e., an $SO_2$ digital word representative of the sensed $SO_2$ level. Such $SO_2$ digital word is then compared, using conventional digital processing techniques, with the data word stored in memory 30 at memory location 66. Based on this comparison, a determination is made as to whether capture exists.

So long as capture is present, there is no need to adjust the energy of the stimulation pulse. However, should capture be lost, then the control logic/processor 40 responds by increasing the energy of the stimulation pulse in an appropriate manner. Typically, this is done by replacing the data word stored in the applicable memory location with a new data word that defines a higher pulse amplitude or a wider pulse width. After several stimulation pulses have been generated at the new (higher) energy level, the sensed $SO_2$ level is again compared to the reference $SO_2$ level to determine if capture has been regained. If capture has been regained, no further adjustments are made to the stimulation energy. If capture has not been regained, then the stimulation energy is again increased, and continues to be increased, in specified increments, until capture is regained. Should capture still not be present at the highest possible stimulation energy, then that is an indication that the current pacemaker operating mode, e.g., VVI, DDD, AVI, etc., is ineffectual. Accordingly, the pacemaker operating mode is switched to an alternate mode, and the stimulation energy is reset to a nominal value.

In some embodiments of the invention, adjustments are made to the stimulation energy both up and down in order to keep the stimulation energy just above the capture threshold (by an appropriate safety margin), thereby conserving the limited energy available from the pacemaker battery. In other embodiments, e.g., as described below in connection with FIG. 3, the stimulation energy is only adjusted up, as required, in order to maintain capture.

It is noted that the control logic/processor 40 of the pacemaker 10 may be realized using appropriate dedicated logic circuitry, and/or a microprocessor circuit. Representative dedicated logic circuitry of the type commonly used in an implantable pacemaker is disclosed in U.S. Pat. No. 4,712,555. Similarly, a pacemaker using a microprocessor to provide the desired control is disclosed in U.S. Pat. No. 4,940,052. Either, or both, of these approaches may be used with the present invention.

Figure 3:
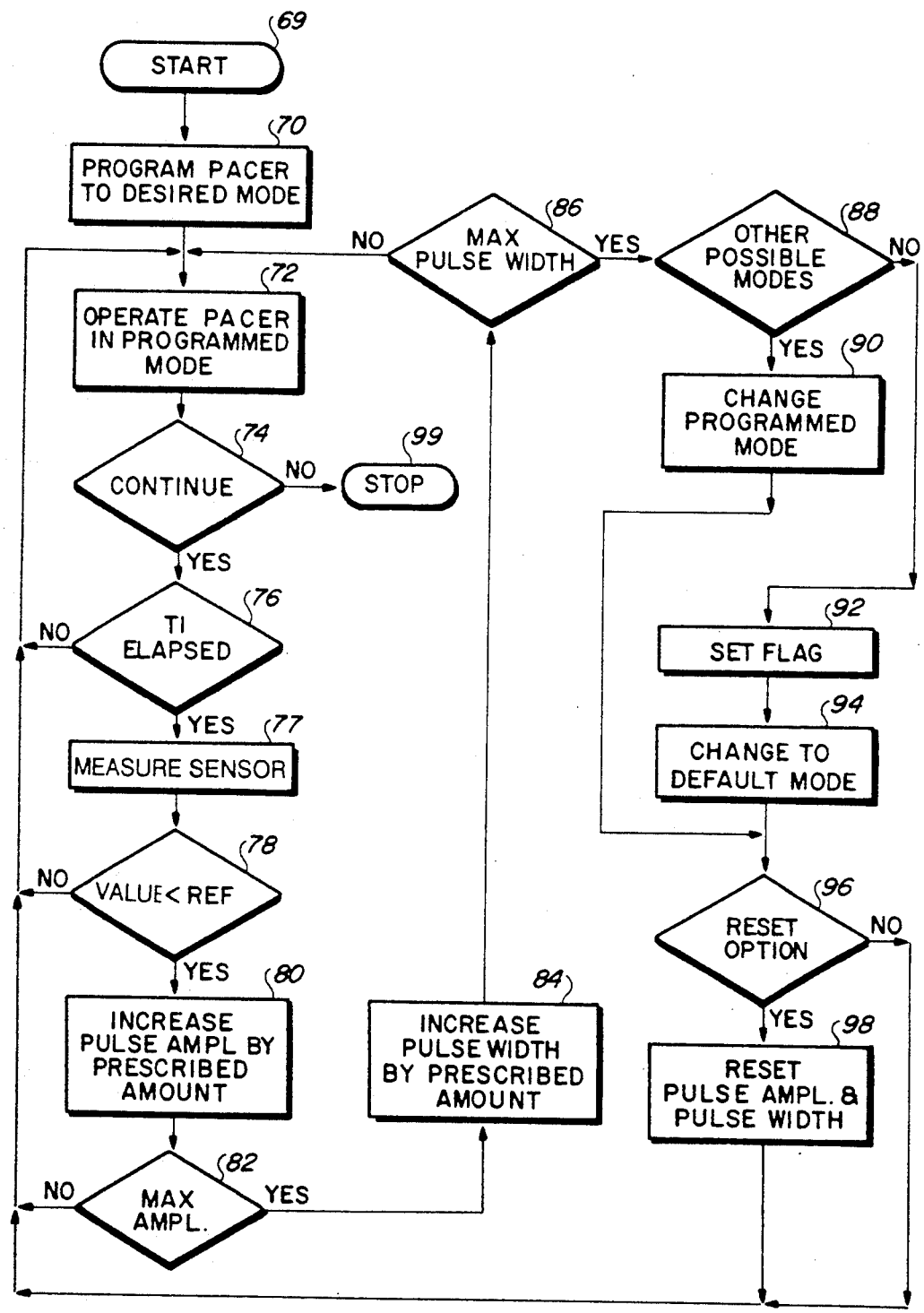
FIG. 3 is a flowchart depicting the processing steps used within the pacemaker control logic/processor of the implantable pacemaker of FIG. 1 in order to change the control parameters of the pacemaker.

Referring next to FIG. 3, a flowchart depicting the processing steps used within the pacemaker control logic/processor 40 of the implantable pacemaker of FIG. 1 to carry out one embodiment of the invention is shown. Those skilled in the art can readily design and/or program the control logic/processor 40 to carry out the steps shown in FIG. 3, or equivalent steps, in order to achieve the desired goal of adjusting the stimulation energy in order to maintain the $SO_2$ level in the blood above a prescribed level, and hence to maintain capture. (In FIG. 3, each step is summarized or shown in a "box" or a "block," with each such box or block having a respective reference number. In the description that follows, reference is made to these steps by their respective block numbers.)

As seen in FIG. 3, after starting the pacemaker (block 69), the pacemaker is programmed to operate in a desired mode of operation (block 70). The available modes of operation of a pacemaker depend upon the particular pacemaker design, and the number and placement of pacing/sensing leads. The operating modes of modern programmable pacemakers are usually referred to by at least a three letter code, e.g., VVI or DDD, where the first letter signifies the chamber of the heart where pacing occurs, the second letter signifies the chamber where sensing occurs, and the third letter signifies how the pacemaker operates (I="inhibits" a stimulation pulse; T=triggers a stimulation pulse; D=dual, or both). A complete description of these codes, and other designations, may be found, e.g., in Furman et al., *A Practice of Cardiac Pacing*, p. 238 (Futura Publishing Co., 1986).

In addition to programming the desired operating mode of the pacemaker, the operating parameters to be used during such programmed mode are also selected. These operating parameters include the initial stimulation energy, as set by selecting an initial pulse amplitude and pulse width. Further, during this initial programming, a reference $SO_2$ level is also selected and programmed into the pacemaker's memory 30, as are numerous other control parameters used by the pacemaker as it operates in its programmed mode in accordance with the invention. These control parameters may include, e.g., the step size or amount of increase (or decrease) in the pulse amplitude or pulse width, the maximum pulse amplitude or pulse width that may exist, the sequence of operating modes that should be invoked in the event capture is lost in the programmed mode and is not able to be regained by increasing the stimulation energy to its maximum level, and a default mode. These and other control parameters may all be programmed into specific memory locations (addresses) of the pacemaker memory 30 in conventional manner.

Once the pacemaker has been programmed to operate in a desired mode, the pacemaker is allowed to operate in such programmed mode (block 72). At any time during such programmed operation, additional programming signals may be sent to the pacemaker in order to stop is programmed operation. Such programming signals may be considered as a form of "interrupt" signal, and the pacemaker logic is configured to always look for the receipt of such signals. In the absence of such an "interrupt" signal, the pacemaker logic assumes that the programmed operation is to continue (block 74). If a programming interrupt signal is received, then the programmed mode of operation stops (block 99). It is noted that as a safety precaution, most pacemakers will not recognize a valid interrupt signal absent a second signal, such as closure of a magnetic reed switch (as can only be accomplished by a physician or other medical personnel having the proper programming equipment).

Assuming that no "interrupt" signals are received, then the programmed mode of operation is allowed to continue for at least a period of T1 seconds (block 76). The value of T1 may be as short as a function of a cardiac cycle. In this case, $SO_2$ will be measured several times each cardiac cycle. T may alternately be set to equal the frequency of the cardiac cycle. Here, $SO_2$ will be measured each cardiac cycle. In still another situation, T1 may be sufficiently long to include several cardiac cycles (a cardiac cycle is the time between successive contractions of the atria or the ventricles). Typically, T1 will be programmed to a value between 200 msec and 5 seconds. A value of T1 that is too short may not afford the patient sufficient time to respond to any adjustments in the stimulation energy that may have been made. A value of T1 that is too long may be dangerous for the patient if capture has been lost. A preferred value of T1 is about once each cardiac cycle.

At the conclusion of the T1 period, the value of $SO_2$ is measured using the $SO_2$ sensor (block 77). If this measured value of $SO_2$ is greater than the reference value of $SO_2$ (block 78), then capture is presumed, and no adjustments are made to the stimulation energy. Thus, the pacemaker continues to operate in its programmed mode of operation for at least another T1 seconds. If the measured $SO_2$ level is less than the $SO_2$ reference level, however, then the stimulation energy is increased. In the embodiment shown in FIG. 3, this stimulation energy is increased by first increasing the pulse width by a prescribed amount (block 80). The prescribed amount may be, for example, a doubling of the pulse width.

After increasing the pulse width by the prescribed amount, a determination is made as to whether the maximum pulse width has been reached (block 82). If not, then the pacemaker operates at the increased stimulation energy (increased pulse width) in the programmed mode of operation for at least another T1 seconds (block 72), after which another $SO_2$ measurement is made (block 77), and a determination is made as to whether the new $SO_2$ measurement is less the $SO_2$ reference (block 78). If the maximum width has been reached (block 82), then the stimulation energy is further increased by increasing the pulse amplitude by a prescribed amount (block 84). For example, the pulse amplitude may be increased by 1.0 msec. Alternatively, the pulse amplitude may be doubled.

After increasing the pulse width by the prescribed amount, a determination is made as to whether the maximum pulse width has been reached (block 86). If not, then the pacemaker operates at the increased stimulation energy (maximum pulse amplitude and increased pulse width) in the programmed mode of operation for at least another T1 seconds (block 72), after which another $SO_2$ measurement is made (block 77), and a determination is made as to whether the new $SO_2$ measurement is less than the $SO_2$ reference (block 78).

If the maximum pulse width has been reached (block 86), then that means the stimulation energy has been increased to its maximum possible level, and capture is still lost. Hence, in accordance with the present invention, the pacemaker mode of operation is changed. A preselected sequence of possible modes of operation is one of the control parameters that may be initially programmed into the pacemaker during initial programming (block 70). Alternatively, a sequence of pacemaker modes of operation may be designed into the pacemaker logic. In either event, once the maximum stimulation energy has been reached in the current mode and capture is still lost, a determination is first made as to whether other possible pacemaker modes of operation may be invoked (block 88), i.e., a determination is made as to what modes of operation of the possible modes have not yet been tried. If not all of the preselected modes have been tried, then the programmed mode of operation is switched to the next mode of the available modes (block 90). Then, depending upon whether a reset option has been selected (block 96), the stimulation energy (pulse amplitude and pulse width) is reset to its initial value (block 98), or not, and the pacemaker operates in the new mode of operation (block 72) for at least a period of T1 seconds after which the level of $SO_2$ in the blood is again measured (block 77), and the process repeats.

If all of the possible modes of operation have been tried, and capture is still lost (block 88), then some means should be used to alert the attending physician of this condition. For the embodiment shown in FIG. 1, this is done by setting a flag (block 92) in the pacemaker logic. This flag may then be downloaded to the programming device 16 at the next checkup of the patient. Further, after setting such a flag, the pacemaker changes to a default mode of operation, selected to best protect the patient (i.e., keep the patient's heart beating). Such a default mode, for most patients, will be a mode that stimulates the patient's heart with a stimulation pulse of maximum energy at a fixed frequency, e.g., 70 beats per minute. If capture has indeed been lost, then such a mode has the best chance of keeping the heart beating and circulating blood through the patient's body. If capture has not been lost, but some other fault has occurred, e.g., the $SO_2$ sensor fails and is not able to sense the correct level of $SO_2$ in the blood, then such a default mode should not harm the patient, yet will still likely be felt by the patient, thereby alerting the patient to visit his or her doctor as soon as possible.

An alternate scheme would be exactly as described above, except that pulse amplitude would be increased first, followed by increasing pulse width. This alternate embodiment is not currently seen as being the preferred implementation.

As described above, it is thus seen that the present invention provides an implantable pacemaker that automatically adjusts the energy of its stimulation pulse only as high as is required to maintain capture, thereby maintaining capture with a minimum expenditure of energy.

As further described above, it is seen that the invention provides a method for determining capture that is easy to implement and inexpensive to carry out; i.e., by simply measuring the $SO_2$ level, and comparing the measured level to a reference level, a quick determination is provided as to whether capture has been lost or not.

As also described above, it is seen that the invention provides a pacemaker having an $SO_2$ sensor, and wherein the pacemaker is configured to automatically adjust the stimulation pulse energy to maintain the level of $SO_2$ in the blood above a preselected level, thereby better maintaining capture, even though the capture threshold of the particular pacemaker patient may change over time. For example, as shown above in FIG. 3, a pacemaker is configured to automatically adjust the stimulation pulse energy in discrete steps in accordance with a preselected pattern that involves: (1) increasing the pulse width of the stimulation pulse in discrete steps up to a maximum value; and (2) if such energy increase is still insufficient to effectuate capture, increasing the amplitude of the stimulation pulse in discrete steps up to a maximum value.

While the invention herein disclosed has been described by means of specific embodiments and applications thereof, numerous modifications and variations could be made thereto by those skilled in the art without departing from the scope of the invention set forth in the claims.

What is claimed is:

1. An implantable pacemaker comprising:
   electronic circuit means housed within an implantable case for generating a stimulation pulse having a prescribed pulse amplitude and pulse width in response to a trigger signal;
   lead means detachably secured to said implantable case and electrically connected to said electronic circuit means for delivering said stimulation pulse to a desired stimulation location of a mammalian heart;
   sensor means for sensing $SO_2$ in blood;
   control means for generating said trigger signal in accordance with a prescribed pacemaker mode of operation, said control means including means for altering the energy of said stimulation pulse by changing at least one of said prescribed pulse amplitude or pulse width as a function of the amount of $SO_2$ sensed by said sensor means.

2. The implantable pacemaker, as set forth in claim 1, wherein said means for altering the energy of said stimulation pulse adjusts the energy of said stimulation pulse as a function of the difference between the amount of $SO_2$ sensed by said sensor means and a preselected reference level at the conclusion of a prescribed time period, said prescribed time period being restarted at the occurrence of each adjustment of the energy of the stimulation pulse.

3. The implantable pacemaker, as set forth in claim 2, wherein said prescribed time period comprises about 15 seconds.

4. The implantable pacemaker, as set forth in claim 3, wherein said adjustment means increases the energy of said stimulation pulse by a prescribed amount in the event that the $SO_2$ sensed by said sensor means is less than said preselected reference level at the conclusion of the prescribed time period.

5. A programmable implantable pacemaker comprising:
   pulse generating means for providing a stimulation pulse on demand, said stimulation pulse having an initial programmed pulse amplitude and pulse width, and hence an initial programmed energy;
   delivery means for delivering said stimulation pulse to at least one of the atrial or ventricular chambers of a mammalian heart in accordance with a programmed mode of operation;
   control means for operating said pacemaker in accordance with said programmed mode of operation;
   sensor means for measuring the $SO_2$ level of the blood within or near said mammalian heart every T1 seconds, where T1 is a programmed timed interval; and
   adjustment means for automatically increasing the programmed energy associated with said stimulation pulse in the event that the measured $SO_2$ level is less than a prescribed reference level at the conclusion of said programmed timed interval;
   whereby the energy of the stimulation pulse is adjusted to be only as high as is necessary to maintain a prescribed level of $SO_2$ in the blood.

6. The programmable implantable pacemaker, as set forth in claim 5, wherein said adjustment means includes means for increasing a selected one of the amplitude or pulse width of the stimulation pulse by a prescribed amount in the event that the measured $SO_2$ level still remains less than the prescribed reference level at the conclusion of each programmed timed interval T1.

7. The programmable implantable pacemaker, as set forth in claim 6, wherein the amplitude or pulse width of the stimulation pulse may be increased by the prescribed amount only up to a programmed maximum level.

8. The programmable implantable pacemaker, as set forth in claim 7, wherein said adjustment means further includes means for increasing the other of said amplitude or pulse width of the stimulation pulse by a prescribed amount at the conclusion of each programmed timed interval T1 in the event that the measured $SO_2$ level still remains less than the prescribed reference after the selected one of the amplitude or pulse width has been increased to its programmed maximum level.

9. The programmable implantable pacemaker, as set forth in claim 8, wherein said control means further includes means for changing the operating mode of said programmable implantable pacemaker in the event that said $SO_2$ level still remains below said prescribed reference level after both said pulse amplitude and pulse width have been increased to their respective maximum levels.

10. The programmable implantable pacemaker, as set forth in claim 9, wherein said adjustment means is for further selectively resetting the values of said pulse amplitude and pulse width after said control means changes said operating mode, whereby the energy of said stimulation pulse may be reset to a prescribed energy upon the changing of the operating mode of said pacemaker.

11. The programmable implantable pacemaker, as set forth in claim 6, wherein the selected one of the pulse amplitude or pulse width that is increased first in response to said $SO_2$ level being less than said reference level comprises the pulse amplitude.

12. The programmable implantable pacemaker, as set forth in claim 11, wherein the prescribed amount by which the pulse amplitude is increased comprises twice its preceding value, whereby the pulse amplitude is doubled at the conclusion of each prescribed timed period T1 if the $SO_2$ level still remains below said prescribed reference level at the conclusion of the prescribed timed period T1.

13. The programmable implantable pacemaker, as set forth in claim 12, wherein the programmed time interval T1 comprises between 200 msec and 5 seconds.

14. The programmable implantable pacemaker, as set forth in claim 6, wherein the selected one of the pulse amplitude or pulse width that is increased first in response to said $SO_2$ level being less than said reference level comprises the pulse width.

15. A method of determining and maintaining capture of a programmable implantable pacemaker with a minimum expenditure of energy, said pacemaker having means for providing a stimulation pulse on demand, said stimulation pulse having an initial programmed pulse amplitude and pulse width, and hence an initial programmed energy, said pacemaker further having means for delivering said stimulation pulse to at least one of the atrial or ventricular chambers of a mammalian heart in accordance with a programmed mode of operation, and said pacemaker further having means for measuring the $SO_2$ level of the blood in or near said mammalian heart, said method comprising the steps of:

(a) operating said pacemaker in accordance with said programmed mode of operation;

(b) measuring the $SO_2$ level of the blood within or near said mammalian heart every T1 seconds, where T1 is a programmed time interval; and (c) automatically increasing the programmed energy associated with said stimulation pulse in the event that the measured $SO_2$ level is less than a prescribed reference level, whereby the energy of the stimulation pulse is adjusted to be only as high as is necessary to maintain a prescribed level of $SO_2$ in the blood.

16. The method, as set forth in claim 15, wherein step (c) comprises increasing a selected one of the amplitude or pulse width of the stimulation pulse by a prescribed amount, repeating steps (a) and (b), and thereafter increasing the selected one of the amplitude or pulse width of the stimulation pulse by the prescribed amount only in the event that the measured $SO_2$ level still remains less than the prescribed reference.

17. The method, as set forth in claim 16, further including continuing to increase the selected one of the amplitude or pulse width of the stimulation pulse by the prescribed amount at the conclusion of each programmed timed interval for so long as the measured $SO_2$ level remains less than the prescribed reference up to a programmed maximum level of said amplitude or pulse width.

18. The method, as set forth in claim 17, further including increasing the other of said amplitude or pulse width of the stimulation pulse by a prescribed amount, repeating steps (a) and (b), and thereafter increasing the other of the amplitude or pulse width of the stimulation pulse by the prescribed amount only in the event that the measured $SO_2$ level still remains less than the prescribed reference.

19. The method, as set forth in claim 18, further including continuing to increase the other of the amplitude or pulse width of the stimulation pulse by the prescribed amount at the conclusion of each programmed timed interval for so long as the measured $SO_2$ level remains less than the prescribed reference up to a programmed maximum level of said amplitude or pulse width.

20. The method, as set forth in claim 19, further comprising changing the operating mode of said programmable implantable pacemaker in the event that said $SO_2$ level still remains below said prescribed reference level after both said pulse amplitude and pulse width have been increased to their maximum levels.

21. The method, as set forth in claim 20, further including selectively resetting the values of said pulse amplitude and pulse width after changing said operating mode to return the energy of said stimulation pulse to a prescribed energy.

22. The method, as set forth in claim 16, wherein the selected one of the pulse amplitude or pulse width that is increased first in response to said $SO_2$ level being less than said reference level is the pulse amplitude.

23. The method, as set forth in claim 22, wherein the step of increasing the pulse amplitude by the prescribed amount comprises doubling the value of the pulse amplitude.

24. The method, as set forth in claim 15, wherein the programmed time interval comprises at least 8 seconds.

25. The method, as set forth in claim 24, wherein the programmed time interval comprises about 15 seconds.

* * * * *